(12) United States Patent  
Bardsley et al.

(10) Patent No.: US 7,923,577 B2  
(45) Date of Patent: Apr. 12, 2011

(54) MENTHYLCARBOXAMIDES AND THEIR USE AS COOLING AGENTS

(75) Inventors: Kathryn Anne Bardsley, Howell, NJ (US); Mark L. Dewis, Matawan, NJ (US); Brian Trevor Grainger, Princeton, NJ (US); Adam Jan Janczuk, Parlin, NJ (US); Arkadiusz Kazimierski, Old Bridge, NJ (US); Kenneth J. Kraut, Union Beach, NJ (US); John L. Sondrup, Jackson, NJ (US); Ying Yang, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 67 days.

(21) Appl. No.: 12/430,585

(22) Filed: Apr. 27, 2009

(65) Prior Publication Data

US 2010/0272655 A1    Oct. 28, 2010

(51) Int. Cl.
  *C07C 233/05* (2006.01)
  *C07C 233/58* (2006.01)
  *A61K 31/16* (2006.01)
  *A61K 31/167* (2006.01)

(52) U.S. Cl. ........ 564/155; 564/168; 514/616; 514/619; 510/119; 424/48; 424/49; 424/65; 424/70.1; 424/73

(58) Field of Classification Search ............... 564/155, 564/168; 514/616, 619; 510/119; 424/48, 424/49, 65, 70.1, 73
See application file for complete search history.

(56) References Cited

U.S. PATENT DOCUMENTS

| 4,150,052 A | 4/1979 | Watson et al. |
| 7,414,152 B2 | 8/2008 | Galopin et al. |
| 2009/0105237 A1 | 4/2009 | Bell et al. |

FOREIGN PATENT DOCUMENTS

| GB | 1351761 | 5/1974 |
| WO | WO 2005/049553 A1 | 6/2005 |

OTHER PUBLICATIONS

Cunningham, D.; Gallaher, E.T.; Grayson, D.H.; McArdle, P.J.; Storey, C.B.; and Wilcock, D.J.; "J. Chem. Society". Perkin Trans. vol. 1, (200) pp. 2692-2698.

*Primary Examiner* — Shailendra Kumar
(74) *Attorney, Agent, or Firm* — Elizabeth M. Quirk; Joseph F. Leightner; Xufan Tseng

(57) ABSTRACT

Described is a new cooling agent represented by Structure I and compositions with known coolers having cooling properties and the application of Structure I in foodstuffs and chewing gum:

Structure I

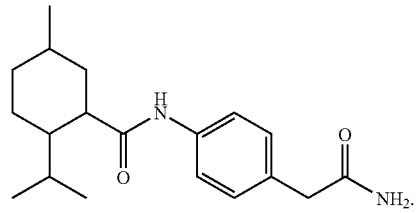

17 Claims, No Drawings

MENTHYLCARBOXAMIDES AND THEIR USE AS COOLING AGENTS

FIELD OF INVENTION

The following invention relates to edible compositions having a unique, long lasting, cooling perception which provides the user with an enhanced perception of breath-freshening without bitterness. The following invention is useful in chewing gum compositions and confectionary compositions which provide a long-lasting, breath freshening perception without bitterness.

BACKGROUND OF THE INVENTION

Cooling agents are describes as chemical compounds providing cold or cool sensations when contacted with the human body, especially with the mucus membranes of the mouth, nose and throat. Cooling compounds are widely used in edible products, beverages, dentifrices, tobacco products, mouthwashes and toiletries.

One class of cooling compounds which are very effective compounds containing an N-substituted p-menthane carboxamide moiety. Examples of these compounds are described in, for example, British Patents GB 1,351,761-2 and U.S. Pat. No. 4,150,052.

Properties of those compounds are based on l-menthol, which is one of the most well-known physiological coolants, and which has been widely used in several applications. L-menthol has an excellent cooling strength and is relatively inexpensive.

It is well recognized that one of the purpose of chewing gum and confectionery products is to enhance ones breath and provide a clean, cool, fresh feeling in the mouth. Unfortunately, most products are not able to maintain such perception for long periods of time, which is a time up to about thirty minutes.

The compound of the present invention may be used alone or in combination with additional compounds or composition which increase cooling and flavor impact and extend these taste effects over a prolonged period of time.

SUMMARY OF THE INVENTION

According to one embodiment of the invention the following Structure is disclosed Structure I

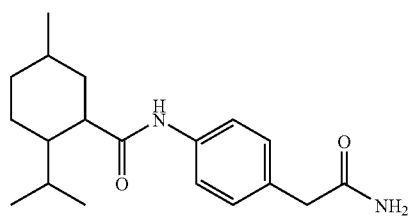

In an additional embodiment the use of Structure I as a cooling composition is disclosed.

In yet a further embodiment of the invention, the combination of Structure I with other compounds and compositions having cooling properties is disclosed.

In still another embodiment a composition is provided containing Structure I.

In yet another embodiment of the invention a composition is provided containing the combination of Structure I with other compounds and compositions having cooling properties.

In another embodiment of the invention an ingestible product for humans or animals which comprises a product base selected from the group consisting of baked goods, dairy products, fruit ices, confectionery products, sugarless candies, jams, jellies, gelatins, puddings, animal feeds, pressed confectionery tablets, hard-boiled candies, pectin-based candies, chewy candies, creme-centered candies, fondants, sugarless hard-boiled candies, sugarless pectin-based candies, sugarless chewy candies, sugarless creme-centered candies, toothpastes, mouthwashes, breath fresheners, carbonated beverages, mineral waters, powdered beverage mixes, other non-alcoholic beverages, cough drops, lozenges, cough mixtures, decongestants, anti-irritants, antacids, anti-indigestion preparations and oral analgesics, and an effective amount of a compound:

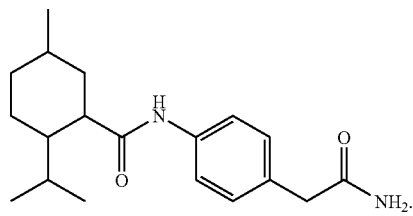

In accordance with a another embodiment of the present invention, a chewing gum composition which is capable of providing long-lasting, breath freshening perception without bitterness comprises a gum base, a sweetener and a cooling composition comprising N-substituted-p-menthane carboxamide of the Structure I:

Structure I

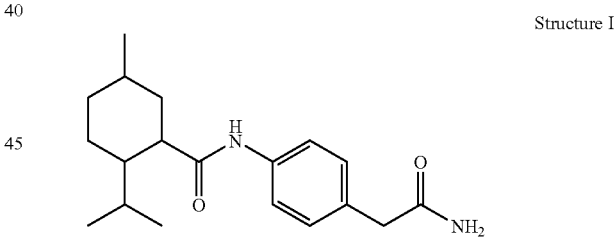

In further embodiments of the invention, a chewing gum composition which is capable of providing long-lasting, breath freshening perception without bitterness comprises a gum base, a sweetener and a cooling composition comprising N-substituted-p-menthane carboxamide of the Structure I in combination with monomenthyl glutarate is disclosed.

In a further embodiment of the invention, a chewing gum composition which is capable of providing long-lasting, breath freshening perception without bitterness comprises a gum base, a sweetener and a cooling composition comprising N-substituted-p-menthane carboxamide of the Structure I in combination with 2-isopropyl-N,2,3-trimethylbutyramid is disclosed.

In yet a further embodiment of the invention, a chewing gum composition which is capable of providing long-lasting, breath freshening perception without bitterness comprises a gum base, a sweetener and a cooling composition comprising N-substituted-p-menthane carboxamide of the Structure I in combination with menthyl acetoacetate is disclosed.

In another embodiment of the invention, a chewing gum composition which is capable of providing long-lasting, breath freshening perception without bitterness comprises a gum base, a sweetener and a cooling composition comprising N-substituted-p-menthane carboxamide of the Structure I in combination with N-ethyl-p-menthanecarboxamide is disclosed.

Another embodiment of the invention is directed to a process for augmenting, enhancing or imparting a taste or cooling or refreshing effect in or to a cosmetic, skin care product, lip gloss, hair care product, cologne, shaving balm, after-shave lotion, dairy product, fruit ice preparation, confectionery, mouth and throat lozenges, cough mixtures, decongestants, antacids, oral analgesics or other medicinal products, chewing gum, candy (including hard candy and soft candy), fondants, toothpaste, mouthwashes, mineral water, alcoholic beverage, non-alcoholic beverage, powdered beverage, or other foodstuff comprising the step of adding to a cosmetic, skin care product, lip gloss, hair care product, cologne, shaving balm, after-shave lotion, dairy product, fruit ice preparation, confectionery, lozenges, cough mixtures, decongestants, antacids, oral analgesics or other medicinal product, chewing gum, candy, fondants, toothpaste, mouthwashes, mineral water, alcoholic beverage, non-alcoholic beverage, powdered beverage, or other foodstuff, a taste or cooling or refreshing effect augmenting, enhancing or imparting quantity and concentration of Structure I:

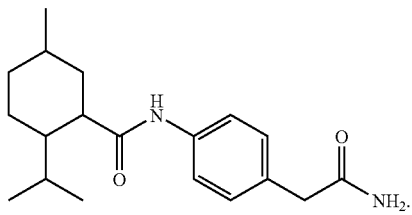

DETAILED DESCRIPTION OF THE INVENTION

Applicants have unexpectedly found that N-substituted-p-menthane carboxamide represented by Structure I, when used by itself or in combination with another coolers such as, but not limited, menthol, menthone, monomenthyl glutarate, 2-isopropyl-N,2,3-trimethylbutyramide, N-ethyl-p-menthanecarboxamide, or menthyl acetoacetate results in an unexpected heightened cooling sensation in edible products.

In a further embodiment of the invention the combination of Structure I with monomenthyl glutarate is disclosed.

In still a further embodiment of the invention the combination of Structure I with 2-isopropyl-N,2,3-trimethylbutyramid is disclosed.

In yet another embodiment of the invention the combination of Structure I with menthyl acetoacetate is disclosed.

In a further embodiment of the invention the combination of Structure I with N-ethyl-p-menthanecarboxamide is disclosed.

In accordance with a another embodiment of the present invention, a chewing gum composition which is capable of providing long-lasting, breath freshening perception without bitterness comprises a gum base, a sweetener and a cooling composition comprising N-substituted-p-menthane carboxamide of the Structure I:

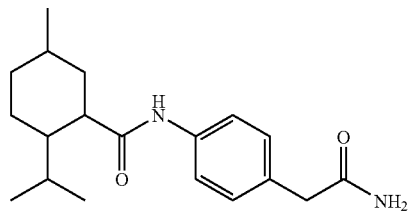

In further embodiments of the invention, a chewing gum composition which is capable of providing long-lasting, breath freshening perception without bitterness comprises a gum base, a sweetener and a cooling composition comprising N-substituted-p-menthane carboxamide of the Structure I in combination with monomenthyl glutarate is disclosed.

In a further embodiment of the invention, a chewing gum composition which is capable of providing long-lasting, breath freshening perception without bitterness comprises a gum base, a sweetener and a cooling composition comprising N-substituted-p-menthane carboxamide of the Structure I in combination with 2-isopropyl-N,2,3-trimethylbutyramid is disclosed.

In yet a further embodiment of the invention, a chewing gum composition which is capable of providing long-lasting, breath freshening perception without bitterness comprises a gum base, a sweetener and a cooling composition comprising N-substituted-p-menthane carboxamide of the Structure I in combination with menthyl acetoacetate is disclosed.

In another embodiment of the invention, a chewing gum composition which is capable of providing long-lasting, breath freshening perception without bitterness comprises a gum base, a sweetener and a cooling composition comprising N-substituted-p-menthane carboxamide of the Structure I in combination with N-ethyl-p-menthanecarboxamide is disclosed.

In another embodiment of the invention an ingestible product for humans or animals which comprises a product base selected from the group consisting of baked goods, dairy products, fruit ices, confectionery products, sugarless candies, jams, jellies, gelatins, puddings, animal feeds, pressed confectionery tablets, hard-boiled candies, pectin-based candies, chewy candies, creme-centered candies, fondants, sugarless hard-boiled candies, sugarless pectin-based candies, sugarless chewy candies, sugarless creme-centered candies, toothpastes, mouthwashes, breath fresheners, carbonated beverages, mineral waters, powdered beverage mixes, other non-alcoholic beverages, cough drops, lozenges, cough mixtures, decongestants, anti-irritants, antacids, anti-indigestion preparations and oral analgesics, and an effective amount of a compound:

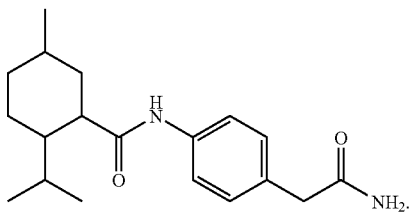

Another embodiment of the invention is directed to a process for augmenting, enhancing or imparting a taste or cooling or refreshing effect in or to a cosmetic, skin care product, lip gloss, hair care product, cologne, shaving balm, after-shave lotion, dairy product, fruit ice preparation, confectionery, mouth and throat lozenges, cough mixtures, decongestants, antacids, oral analgesics or other medicinal products, chewing gum, candy (including hard candy and soft candy), fondants, toothpaste, mouthwashes, mineral water, alcoholic beverage, non-alcoholic beverage, powdered beverage, or other foodstuff comprising the step of adding to a cosmetic, skin care product, lip gloss, hair care product, cologne, shaving balm, after-shave lotion, dairy product, fruit ice preparation, confectionery, lozenges, cough mixtures, decongestants, antacids, oral analgesics or other medicinal product, chewing gum, candy, fondants, toothpaste, mouthwashes, mineral water, alcoholic beverage, non-alcoholic beverage, powdered beverage, or other foodstuff, a taste or cooling or refreshing effect augmenting, enhancing or imparting quantity and concentration of Structure I:

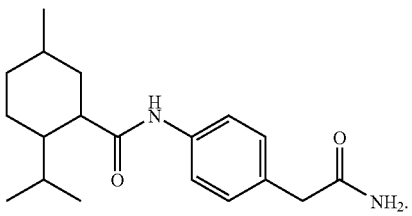

Structure I possesses the following flavor properties when tasted in water at 10 ppm and at 1 ppm:

At the level of 10 ppm in water this material contributes moderate throat and mouth cooling that lingers with some bitter notes in background. Cooling lasts with breath in for 30 minutes.

At the level of 1 ppm in water Structure I is clean with slight cooling up front that builds with time to moderate level. Cooling lasted for 30 minutes.

Based on this flavor evaluation, it is indicative that the Structure I of our invention are useful for augmenting, enhancing or imparting a taste or cooling or refreshing effect in or to a cosmetic, skin care product, lip gloss, hair care product, cologne, shaving balm, after-shave lotion, dairy product, fruit ice preparation, confectionery, mouth and throat lozenges, cough mixtures, decongestants, antacids, oral analgesics or other medicinal products, chewing gum, candy (including hard candy and soft candy), fondants, toothpaste, mouthwashes, mineral water, alcoholic beverage, non-alcoholic beverage, powdered beverage, or other foodstuff as a result of adding to a cosmetic, skin care product, lip gloss, hair care product, cologne, shaving balm, after-shave lotion, dairy product, fruit ice preparation, confectionery, lozenges, cough mixtures, decongestants, antacids, oral analgesics or other medicinal product, chewing gum, candy, fondants, toothpaste, mouthwashes, mineral water, alcoholic beverage, non-alcoholic beverage, powdered beverage, or other foodstuff, a taste or cooling or refreshing effect augmenting, enhancing or imparting quantity and concentration of Structure I.

As used herein the term, olfactory effective amount is understood to mean the amount of compound in flavor compositions, oral care compositions and articles, nasal care compositions and articles, skin care compositions, hair care compositions, cosmetic compositions, and other consumable materials as defined herein, the individual component will contribute to its particular olfactory characteristics, but the flavor, taste and aroma effect on the overall composition will be the sum of the effects of each of the cooling and/or refreshing and/or pungent flavor and/or sense imparting, augmenting or enhancing ingredients. As used herein taste effects include cooling, refreshing and pungent effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The preferred usage level of Structure I used in products is at a level from about 0.001 to about 1 weight percent (%) and more preferably 0.015 to about 0.15 weight percent and most preferably about 0.04 weight percent.

The usage levels of Structure I vary depending on the product in which the Structure I is employed.

Thus, with reference to the use of Structure I of our invention in alcoholic beverages, the usage level is from about 0.0005 to about 0.02 weight percent, preferably from about 0.002 to about 0.0150 weight percent and most preferably from about 0.0030 to about 0.0080 weight percent.

With reference to the use of the Structure I of our invention in non-alcoholic beverages including carbonated beverages and fruit drinks, the non-alcoholic beverages are flavored at levels of from about 0.0001 to about 0.0030 weight percent, preferably from about 0.0005 to about 0.0015 weight percent.

With reference to the use of the Structure I of our invention in toothpaste, the toothpaste can be satisfactorily flavored by using Structure I at levels of from about 0.02 to about 0.07 weight percent, more preferably from about 0.03 to about 0.06 weight percent and most preferable from about 0.035 up to about 0.055 weight percent.

With reference to the use of the Structure I of our invention in candy products including hard candy, the candy can be flavored at levels of from about 0.05 to about 0.25 weight percent; preferably from about 0.1 to about 0.2 weight percent.

With reference to the use of the Structure I of our invention in chewing gum, chewing gum usage levels are from about 0.01 to about 1 weight percent, preferably from about 0.1 to about 0.5 weight percent and more preferably from about 0.15 to about 0.25 weight percent.

When used in combination with other cooling compounds and compositions one skilled in the art may modify the levels to achieve the desired result.

When used in combination with other cooling compounds and compositions Structure I may be used at a level from about 0.01 to about 0.2 weight percent.

Specifically, when used in combination with Structure I, monomenthyl glutarate may be used at a level from about 0.1 to about 1 weight percent and more preferably from about 0.25 to about 0.4 weight percent.

A preferred level of 2-isopropyl-N,2,3-trimethylbutyramid when used in combination with Structure I is from about 0.01 to about 1 weight percent and more preferably from about 0.03 to about 0.3 weight percent.

A preferred level of menthyl acetoacetate when used in combination with Structure I is from about 0.02 to about 1.0 weight percent and more preferably from about 0.2 to about 0.6 weight percent.

A preferred level of N-ethyl-p-menthanecarboxamide when used in combination with Structure I is from about 0.02 to about 0.5 weight percent and more preferably from about 0.05 to about 0.2 weight percent.

The term foodstuff as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When Structure I is used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with Structure I; (2) that they be organoleptically compatible with the Structure I of our invention whereby the flavor of the ultimate consumable material to which Structure I is added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the menthyl half acid esters or N-alkyl alkamic acid menthyl esters of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimeth-oxyphenol; amyl acetate; amyl cinnamate; γ-butyryl lactone; furfural; trimethylpyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methylpyrazine; 2-ethyl-3-methylpyrazine; tetramethylpyrazine; polysulfides; dipropyl disulfide; methyl benzyl disulfide; alkyl thiophene; 2,3-dimethyl thiophene; 5-methyl furfural; acetyl furan; 2,4-decadienal; guaiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethylpyrazine; propyl propenyl disulfide; propyl propenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolne; and 4-methyl-2-(methylthiomethyl)-1,3-dithiolane. These and other flavor ingredients are provided in U.S. Pat. Nos. 6,110,520 and 6,333,180.

Structure I or compositions incorporating them, as mentioned above can be combined with one or more vehicles or carriers for adding them to the particular product. Vehicles can be water-soluble or oil-soluble; and can be edible or otherwise suitable materials such as ethyl alcohol, propylene glycol, water, triacetin, vegetable oil, triethyl citrate and the like, as described supra. Carriers include materials such as gum arabic, carrageenan, xanthan gum, guar gum and the like.

Structure I prepared according to our invention can be incorporated with the carriers by conventional means such as spray-drying, extrusion, drum-drying and the like. Such carriers can also include materials for coacervating the menthyl half-acid ester derivatives including menthyl half acid esters or N-alkyl alkamic acid menthyl esters of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of Structure I utilized should be sufficient to impart the desired flavor characteristic to the product, but on the other hand, the use of an excessive amount of Structure I is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology effective amount and sufficient amount is understood in the context of the present invention to be quantitatively adequate to alter the flavor of the foodstuff.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

Example 1

Preparation of 4-Aminophenylacetamide

The 4-aminophenylacetamide used in this example was obtained according to patent literature WO 02/08247 A2 or WO 03/051909 A2. Procedure was as follows: Methanol (200 mL) was charged to 4-aminophenylacetic acid (Aldrich) (25 g, 0.165 mol). Sulfuric acid (18 mL concentrated, 0.648 mol) was added maintaining the temperature <20° C. The mixture was then refluxed for one hour and concentrated by distillation at atmospheric pressure until the volume of 140 mL. The mixture was then cooled to 50° C. and tert-buthyl methyl ether (300 mL) was added maintaining the temperature above 45° C. The mixture was gradually cooled to 0-5° C. and held at this temperature for 1 hour. The resultant crystalline product was isolated by filtration and washed with cold methanol: tert-butyl methyl ether (20 mL: 55 mL) and cold tert-butyl methyl ether and then dried under vacuum to give methyl 4-aminophenylacetate hydrogensulfate (35.3 g, 80% yield).

Obtained compound was added to 20% w/w aqueous NaCl (65 mL). Aqueous ammonia (90 mL), containing dissolved sodium chloride (15 g) was added maintaining the temperature 15-25° C. The mixture was then stirred for 16 hours at 22° C. The mixture was cooled to 0-5° C. and held at this temperature for one hour. The resultant crystalline product was isolated by filtration, washed with water (2×30 mL) and dried under vacuum at 45° C. giving 13.6 g of product, 68% yield.

Preparation of (2S,5R)—N-[4-(2-Amino-2-oxoethyl) phenyl]-5-methyl-2-(propan-2-yl)cyclohexanecarboxamide The p-Menthane-3-carboxylic acid (obtained according to publication: Desmond Cunningham, Eva T. Gallagher, David H. Grayson, Patrick J. McArdle, Christina B. Storey, Deborah J. Wilcock; *J. Chem. Soc., Perkin Trans.* 1, 2002, 2692-2698), (2.5 g, 13.5 mmol) was heated under reflux with thionyl chloride (Alfa Aesar) (7 mL) for three hours. Then the excess of thionyl chloride was distilled off in vacuo. Residue was dissolved in $CH_2Cl_2$ (30 mL). This solution was added drop wise to the mixture of 4-aminophenylacetamide (2.2 g, 13.5 mmol) and triethylamine (1.8 g, 17.8 mmol) at 0° C. After ten minutes the solution was allowed to warm to room temperature. After 1 hour GC showed that reaction is completed. $CH_2Cl_2$ (50 mL) was added to the reaction and this mixture was washed by 0.1 N HCl aq, water, 0.1 N NaOH aq, by brine and dried over $MgSO_4$. The mixture was then filtrated and evaporated give white solid which was crystallized from hot ethyl acetate providing 3 g (65%) product as white solid. $C_{19}H_{28}N_2O_2$ (MW 316.22); $^1H$ NMR (500 MHz, DMSO-d6) δ: 9.79 (s, 1H), 7.51 (d, 2H, J=8.41), 7.36 (br s, 1H), 7.15 (d, 2H, J=8.41 Hz), 6.82 (br s, 1H), 3.30 (s, 2H), 2.30 (t, 1H, J=11.43 Hz of d, J=3.19 Hz), 1.70-1.77 (m, 2H), 1.61-1.68 (m, 2H), 1.51 (t, 1H, J=11.5 Hz, of t, J=2.8 Hz), 1.33-1.38 (brs, 1H), 1.17 (q, 1H, J=12.16 Hz), 1.02 (q, 1H, J=12.7 Hz, of d, J=2.7 Hz) 0.89-0.96 (m, 1H), 0.88 (d, 3H, J=6.5 Hz), 0.85 (d, 3H, J=6.9 Hz), 0.79 (d, 3H, J=6.9 Hz).

Flavor Evaluation of Structure I

At the level of 10 ppm in water this material contributes moderate throat and mouth cooling that lingers with some bitter notes in background. Cooling lasts with breath in for 30 minutes.

At the level of 1 ppm in water Structure I is clean with slight cooling up front that builds with time to moderate level. Cooling lasted for 30 minutes.

Example 2

Preparation of a Chewing Gum

The following gum base formulation was prepared:

TABLE I

| Ingredients | Parts by Percentage (%) | Parts by Weight (grams) |
| --- | --- | --- |
| Gum Base, Hades-T | 29.35 | 205.45 |
| Maltitol Syrup | 3.00 | 21 |
| Sorbitol Powder | 48.30 | 338.1 |
| Mannitol Powder | 8.00 | 56 |
| Glycerin | 9.00 | 63 |
| Sucralose | 0.20 | 1.4 |
| Acesulfame K | 0.15 | 1.05 |
| Cherry Flavor | 1.00 | 7 |
| Total | 99.00 | 693 |

The cherry flavor is commercially available from IFF. The gum base, Hades-T is commercially available from Cafosa Gum, Barcelona Spain.

Structure I by itself and in separate mixtures with monomenthyl glutarate, 2-isopropyl-N,2,3-trimethylbutyramid, N-ethyl-p-menthanecarboxamide and menthyl acetoacetate at levels detailed in the Tables below was blended with the gum base in a Sigma mixer. The resultant chewing gum blend was then manufactured into strips 1 inch in width and 0.1 inches in thickness. These strips were cut into lengths of 3 inches each. A control gum, without any coolers, was also manufactures into strips and this control gum exhibited a flavor without imparting any cooling effect.

The resulting gum blends had a substantially identical to the taste profile of the control gum; however the gum blends had cooling effects as described below.

Samples were profiled by a highly trained descriptive analysis panel. The ballot consisted of the following terms: Total impact, total mint, cooling-mouth closed, cooling-breath in, nasal cooling—breath in, throat irritation, bitterness, tongue irritation, numbing. Each attribute was rated at discrete time points including 5 secs, 30 secs, 90 secs, 3 mins, 5 mins, 7 mins, 10 mins, 15 mins, 20 mins, and 30 mins.

| Gum Blended with Structure I |
| --- |
| Panelist 1 |
| 11:04 Start |
| 11:05 Bitter, Brown, Sweet, slightly Vanilla |
| 11:06 Start to notice cooling |
| 11:08 Moderate cooling |
| 11:11 Moderate cooling in mouth and now back of the throat; nice on breath in |
| 11:11 Continued long lasting cooling |
| 11:15 Slight cooling moving to the front of the mouth |
| 11:18 Stable cooling all over, nice level |
| 11:22 Long lasting |
| Panelist 2 |
| 11:04 Start, Very sweet, brown |
| 11:07 Started to notice cooling on breath and tip of the tongue |
| 11:09 Started to notice on back of throat, continued to build in the rest of the mouth |
| 11:11 Cooling consistent throughout mouth, slight irritation on the back of the throat |
| 11:15 Cooling level the same |
| 11:24 Still getting a good amount of cooling |
| 12:07 Cooling is gone |

-continued

Gum Blended with Structure I

Panelist 3

11:04 Start
11:07 Cooling on the back of the throat
11:14 Concentrated on the back of the throat; irritating
11:22 Full cooling after 20 min Panelist 4

11:04 Start
11:07 Cooling perception begins (mild)
11:09 Cooling pleasant, builds to moderate cooling on the front/ tip of tongue
11:11 Intensity max reached
11:14 Cooling plateau, maintained. Delocalized all over mouth
11:19 Remains intense
11:20 Moves to throat (mild) very intense on tip of the tongue and center
11:24 Still cooling
12:00 Cooling remains
12:15 Cooling diminished significantly The following table details the panelist's results for the combination of Structure I with monomenthyl glutarate, 2-isopropyl-N,2,3-trimethylbutyramid, N-ethyl-p-menthanecarboxamide and menthyl acetoacetate at 3 minutes, 8 minutes, 20 minutes and 30 minute, 40 minute and 50 minute intervals. The amounts are listed in weight percent.

What is claimed:
1. A compound:

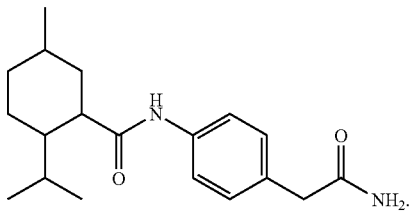

2. A composition selected from topical products for humans and animals, oral care products, nasal care products, and chewing gum which comprises a product base and an effective amount of the compound of claim 1.

3. A composition as claimed in claim 1 which comprises from 0.001-1.0% by weight, based on the total weight of the composition, of said coolant.

4. A composition comprising a product base selected from the group consisting of baked goods, dairy products, fruit ices, confectionery products, sugarless candies, jams, jellies, gelatins, puddings, animal feeds, pressed confectionery tablets, hard-boiled candies, pectin-based candies, chewy candies, creme-centered candies, fondants, sugarless hard-boiled

TABLE II

|   | Structure I | monomenthyl glutarate | 2-isopropyl-N,2,3-trimethylbutyramid | N-ethyl-p-menthanecarboxamide | menthyl acetoacetate | Comments |
|---|---|---|---|---|---|---|
| 1 | 0.036 | 0.12 | | | | 3 minutes: clean, moderate cooling.<br>8 minutes: mild but pleasant cooling.<br>20 minutes: more cooling in throat than in mouth. Nice on breathe in. Expectorate.<br>30 minutes: minimal cooling in throat. |
| 2 | 0.036 | | 0.06 | | | 3 minutes: sharp cooling on tip of tongue and in throat.<br>8 minutes: cooling more intense than #1 & #5.<br>20 minutes: pleasant cooling, still quite strong.<br>30 minutes: still cool. Better cooling experienced than in #1 & #5. Expectorate |
| 3 | 0.036 | | | 0.044 | | 3 minutes: pleasant cooling. Strong on tip of tongue. Salivating.<br>8 minutes: moderate cooling delocalized all over tongue.<br>20 minutes: still cooling on tongue and roof of mouth towards the back.<br>30 minutes: more cooling in roof of mouth than the back and in throat.<br>40 minutes: cooling in roof of mouth towards the back and in throat. Cooling on breathe in. Expectorate.<br>50 minutes: lingering cooling. |
| 4 | 0.036 | | | | 0.06 | 3 minutes: cooling delocalized, not intense, fairly mild. Cooling accumulating in nasal cavity.<br>8 minutes: coolness building. Cooling delocalized with some concentration on tip of tongue.<br>20 minutes: cooling intensified. Pleasant cooling especially in back of throat.<br>30 minutes: cooling localized in throat. Moderate cooling on center of tongue.<br>40 minutes: more intense than at 30 minutes. Cooling on front of tongue and in throat.<br>50 minutes: minimal cooling. After one hour, significant residual cooling on sides of tongue and in throat. | candies, sugarless pectin-based candies, sugarless chewy candies, sugarless creme-centered candies, toothpastes, mouthwashes, breath fresheners, carbonated beverages, mineral waters, powdered beverage mixes, other non-alcoholic beverages, cough drops, lozenges, cough mixtures, decongestants, anti-irritants, antacids, anti-indigestion preparations and oral analgesics, and an effective amount of a compound:

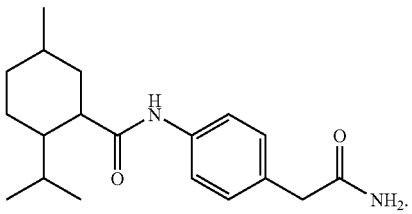

5. A composition as claimed in claim 4 wherein the orally ingested products are selected from lozenges, cough mixtures, decongestants, anti-irritants, antacids, anti-indigestion preparations and oral analgesics.

6. A coolant composition which comprises an effective amount of the compound of claim 1 and at least one secondary coolant component selected from the group consisting of menthol, menthone, monomenthyl glutarate, 2-isopropyl-N,2,3-trimethylbutyramide, N-ethyl-p-menthanecarboxamide, menthyl acetoacetate and mixtures thereof.

7. A composition as claimed in claim 4 wherein the ingestible product is a foodstuff selected from the group consisting of baked goods, dairy products, fruit ices, confectionery products, sugarless candies, jams, jellies, gelatins, puddings and animal feeds.

8. A composition as claimed in claim 4 wherein the topical product is selected from the group consisting of face creams, talcum powders, hair oils, shampoos, bath oils, bath salts, toilet soaps, colognes, antiperspirants, toilet water, perfume, shaving lotion, shaving cream, hair tonic, ointments and lotions.

9. A composition as claimed in claim 4 wherein the oral care product is selected from dentifrices and mouthwashes.

10. A composition as claimed in claim 4 wherein the ingestible product is cough drops.

11. A composition as claimed in claim 4 which comprises from 0.001-1.0% by weight, based on the total weight of the composition, of said coolant.

12. A composition as claimed in claim 4 additionally comprising at least one secondary coolant component selected from the group consisting of menthol, menthone, monomenthyl glutarate, 2-isopropyl-N,2,3-trimethylbutyramide, N-ethyl-p-menthanecarboxamide, menthyl acetoacetate and mixtures thereof.

13. A composition as claimed in claim 4 wherein said composition is selected from pressed confectionery tablets, hard boiled candies, pectin-based candies, chewy candies, cream-centered candies, fondants, sugarless hard-boiled candies, sugarless pectin-based candies, sugarless chewy candies, sugarless cream-centered candies, animal feeds, breath fresheners, carbonated beverages, mineral waters, powdered beverage mixes and non-alcoholic beverages.

14. A process for augmenting, enhancing or imparting a taste or cooling or refreshing effect in or to a cosmetic, skin care product, lip gloss, hair care product, cologne, shaving balm, after-shave lotion, dairy product, fruit ice preparation, confectionery, mouth and throat lozenges, cough mixtures, decongestants, antacids, oral analgesics or other medicinal products, chewing gum, candy, fondants, toothpaste, mouthwashes, mineral water, alcoholic beverage, non-alcoholic beverage, powdered beverage, or other foodstuff comprising the step of adding to a cosmetic, skin care product, lip gloss, hair care product, cologne, shaving balm, after-shave lotion, dairy product, fruit ice preparation, confectionery, lozenges, cough mixtures, decongestants, antacids, oral analgesics or other medicinal product, chewing gum, candy, fondants, toothpaste, mouthwashes, mineral water, alcoholic beverage, non-alcoholic beverage, powdered beverage, or other foodstuff, a taste or cooling or refreshing effect augmenting, enhancing or imparting quantity and concentration of Structure I:

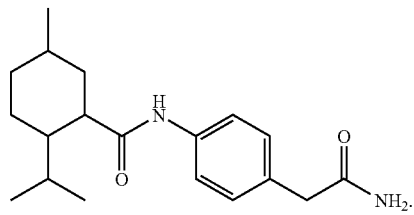

15. The process of claim 14 additionally comprising at least one secondary coolant component selected from the group consisting of menthol, menthone, monomenthyl glutarate, 2-isopropyl-N,2,3-trimethylbutyramide, N-ethyl-p-menthanecarboxamide, menthyl acetoacetate and mixtures thereof.

16. A chewing gum composition comprising a gum base, a sweetener and N-substituted-p-menthane carboxamide of the following Structure I:

Structure I

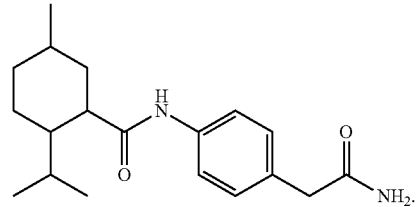

17. The chewing gum composition of claim 16 additionally comprising at least one secondary coolant component selected from the group consisting of menthol, menthone, monomenthyl glutarate, 2-isopropyl-N,2,3-trimethylbutyramide, N-ethyl-p-menthanecarboxamide, menthyl acetoacetate and mixtures thereof.

\* \* \* \* \*